US00PP27038P2

(12) United States Plant Patent
Korlipara

(10) Patent No.: US PP27,038 P2
(45) Date of Patent: Aug. 9, 2016

(54) ***LEUCANTHEMUM* PLANT NAMED 'BELGIAN LACE'**

(50) Latin Name: *Leucanthemum×superbum*
Varietal Denomination: Belgian Lace

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 4 days.

(21) Appl. No.: 14/544,792

(22) Filed: Feb. 18, 2015

(51) Int. Cl.
*A01H 5/02* (2006.01)

(52) U.S. Cl.
USPC ..... Plt./285

(58) Field of Classification Search
USPC ..... Plt./285
CPC ..... A01H 5/025
See application file for complete search history.

(56) References Cited

PUBLICATIONS http://www.greenhousegrower.com/varieties/terra-nova-nurseries-introduces-new-leucanthemum-variety/; Nov. 11, 2014; 6 pages.*

* cited by examiner

*Primary Examiner* — Kent L Bell
(74) *Attorney, Agent, or Firm* — Klarquist Sparkman, LLP

(57) ABSTRACT

A new and distinct *Leucanthemum* plant named 'Belgian Lace' characterized by double daisy type inflorescences, yellow flower buds and young ray florets, fully open inflorescences that display numerous white ray florets with frilly tips around a large gold disc, excellent bloom size, an extremely low, compact habit, and excellent vigor.

1 Drawing Sheet

Botanical denomination: *Leucanthemum×superbum.*
Variety designation: 'Belgian Lace'.

BACKGROUND OF THE INVENTION

The present invention relates to a new and distinct cultivar of *Leucanthemum×superbum* and given the cultivar name 'Belgian Lace'. *Leucanthemum* is in the family Asteraceae. This new cultivar originated from a controlled cross between unnamed, proprietary *Leucanthemum×superbum* seedlings. The seed of many crosses was massed so the exact parents are unknown.

Compared to *Leucanthemum* 'Bridal Bouquet', U.S. Plant Pat. No. 24,260, the new cultivar is shorter and the inflorescences are more yellow and more double.

SUMMARY OF THE INVENTION

This new *Leucanthemum* cultivar is distinguished as unique with its:

1. double daisy type inflorescences,
2. yellow flower buds and young ray florets,
3. fully open inflorescences that display numerous white ray florets with frilly tips around a large gold disc,
4. excellent bloom size,
5. an extremely low, compact habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 1-and-a-half-year-old plant growing in the ground in full sun in the trial field (in front of a black background) in mid-June in Canby, Oreg.

FIG. 2 shows a close up on the inflorescences.

DETAILED PLANT DESCRIPTION

The following is a detailed description of the new *Leucanthemum* cultivar based on observations of 1-and-a-half-year-old specimens growing in the field in full sun under typical outdoor conditions in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The Royal Horticultural Society Colour Chart, $5^{th}$ edition, 2007.

Plant:

*Type.*—Herbaceous perennial.
*Hardiness.*—USDA Zones 5 to 9.
*Size.*—42 cm wide and 28 cm tall to top of inflorescences.
*Form.*—Basal clump.
*# crowns.*—14.
*Vigor.*—Excellent.

Stem (flowering):

*Type.*—Ascending with thick, strong stems.

*Number of stems*.—About 14 stems from the crown, each flowering with 1 to 4 inflorescences per stem.

*Size*.—Grows to about 24 cm tall to a terminal inflorescence and 6 mm wide at base.

*Internode length*.—8 mm to 12 mm.

*Surface texture*.—Pubescent.

*Color*.—Green 137A.

Leaves:

*Type*.—Simple.

*Shape*.—Lanceolate.

*Arrangement*.—Alternate.

*Blade size*.—Grows to 8.5 cm long and 22 mm wide.

*Margins*.—Coarsely serrate.

*Apex*.—Acute.

*Base*.—Clasping.

*Surface texture*.—Pubescent on both sides.

*Venation*.—Pinnate.

*Petiole*.—Sessile.

*Color*.—Topside Green N137A with main vein Yellow Green 147C, bottom side Yellow Green 147B with main vein Yellow Green 147C.

Inflorescence:

*Type*.—Composite on terminal stalked heads.

*Number of inflorescences per plant*.—About 39.

*Size*.—Grows to 9.5 cm wide and 4 cm deep.

*Form*.—Ray florets held upright when young, lower ray florets reflex down with maturity, mature disc is mostly flat.

*Bud* (*immature inflorescence*).—18 mm wide and 2 cm deep, ray florets held vertically and cupped inwards, Yellow 7A on top blending to 2D on the bottom.

*Ray florets*.—With 1 pistil and no stamen, about 160 in number (about 10 smaller size near the disc florets), oblong, tip 3 lobed (lobes 1 mm long to frilly and cut to base), margins entire, base attenuate, average size 4.5 cm long and 7 mm wide, glabrous on both sides; limb 1.5 to 4 cm long, top and bottom side Yellow 4C with tips 4A when young changing to White NN155B; claw 4 mm long and 2 mm wide, Yellow Green 144B; pistil 7 mm long, ovary 2 mm long, Yellow Green 145D, style 4 mm long, Yellow Green 145D, 2 branched stigma 0.5 mm long, Yellow 7A.

*Disc*.—Slightly concave becoming flat, becoming 10 mm deep and 30 mm wide with maturity, Yellow Orange 16A.

*Disc florets*.—About 370 in number, each 9 mm long and 1.3 mm wide; corolla tubular campanulate, 7 mm long and 1.5 mm wide, 5 lobed, glabrous, Yellow 13A on top half and Yellow Green 145A on the bottom half; pistil 1, 6 mm long, ovary 2 mm long and Yellow Green 145D, style 3.5 mm long, Greyed Yellow 160B, 2 branched stigma 0.5 mm long, Greyed Yellow 160B; stamen 5 in number, 5 mm long, filaments 2 mm long, Yellow Green 150D, anthers 3 mm Yellow Orange 17A, pollen Yellow Orange 21A.

*Involucral bracts*.—About 50 in number, in 3 imbricate whorls, area 3.3 cm wide and 10 mm deep, lobes lanceolate, grow to 11 mm long and 4 mm wide, Green 137A, margin thin and somewhat transparent, Greyed Purple 187A, tip acute, glabrous.

*Receptacle*.—Grows to 20 mm wide and 5 mm deep, Yellow Green 145C.

*Bloom period*.—June through July in Canby, Oreg.

*Fragrance*.—None.

*Lastingness*.—Each inflorescence lasts about three weeks in Canby, Oreg.

Seeds: None seen.

*Fertility*.—Low.

Disease and pests: The new cultivar is typical to the genus. No known resistances to pests or diseases. No problems have been found in Canby, Oreg.

I claim:

1. A new and distinct *Leucanthemum* plant as herein illustrated and described.

* * * * *

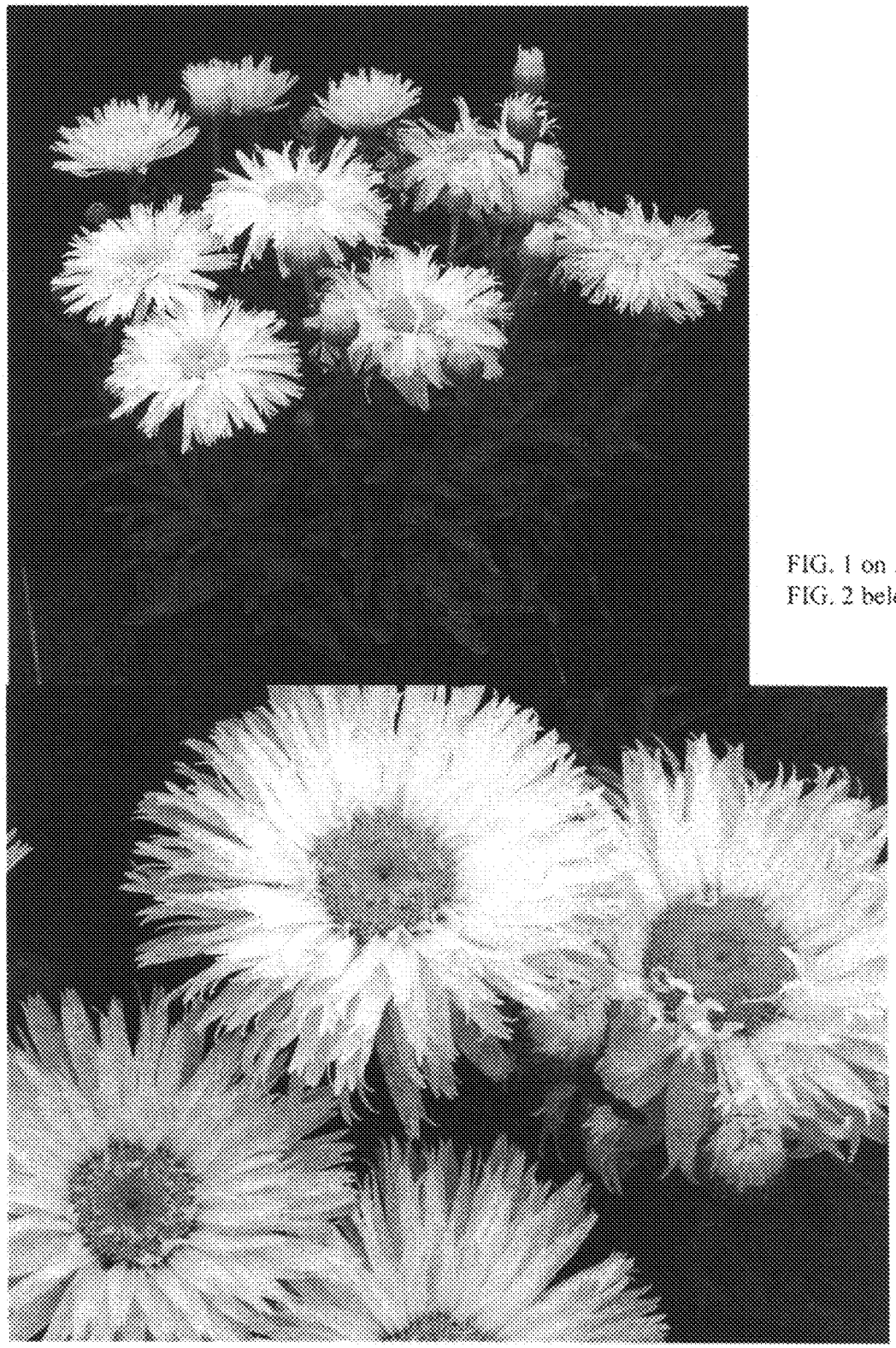
FIG. 1 on left,
FIG. 2 below